United States Patent [19]

Talbot et al.

[11] Patent Number: 4,587,427
[45] Date of Patent: May 6, 1986

[54] BREATH ANALYZER

[75] Inventors: Douglas C. Talbot, Vail; James L. Witler, Avon, both of Colo.

[73] Assignee: CMI, Inc., Minturn, Colo.

[21] Appl. No.: 517,920

[22] Filed: Jul. 28, 1983

[51] Int. Cl.$^4$ .................................. G01N 21/35
[52] U.S. Cl. ............................... 250/339; 250/343
[58] Field of Search ..................... 250/339, 343–346, 250/373; 422/84; 356/437; 128/719

[56] References Cited

U.S. PATENT DOCUMENTS

| Re. 31,246 | 5/1983 | Adrian et al. | 250/344 |
|---|---|---|---|
| 3,544,789 | 12/1970 | Wieder | 250/373 |
| 3,562,524 | 2/1971 | Moore et al. | 250/343 |
| 3,860,344 | 1/1975 | Garfunkel | 250/345 |
| 4,268,751 | 5/1981 | Fritzlen et al. | 250/343 |
| 4,314,564 | 2/1982 | Albarda | 128/719 |
| 4,355,233 | 10/1982 | Warnke et al. | 250/343 |
| 4,363,635 | 12/1982 | Hutson | 250/343 |

Primary Examiner—Carolyn E. Fields
Attorney, Agent, or Firm—Charles F. Pigott, Jr.

[57] ABSTRACT

A method and apparatus for determining the concentration of a predetermined energy absorbing compound in a breath sample even in the presence of other unknown energy absorbing compounds. Infrared energy of three wavelengths are passed through the collected sample. The first wavelength of infrared energy, 3.95 microns for example, is selected to be insensitive to absorption by both the predetermined energy absorbing compound such as ethanol and the unknown energy absorbing compounds such as acetone and water vapor. The second wavelength of infrared energy, 3.48 microns for example, is selected to be significantly absorbed by ethanol. The third wavelength of infrared energy, 3.39 microns for example, is selected to be significantly absorbed by acetone and water vapor. Operational amplifiers responsive to the first, second and third predetermined wavelengths of energy are utilized to subtract the effect of the absorption by acetone and water vapor so as to generate an electrical output signal which is proportional only to the ethanol concentration.

32 Claims, 7 Drawing Figures

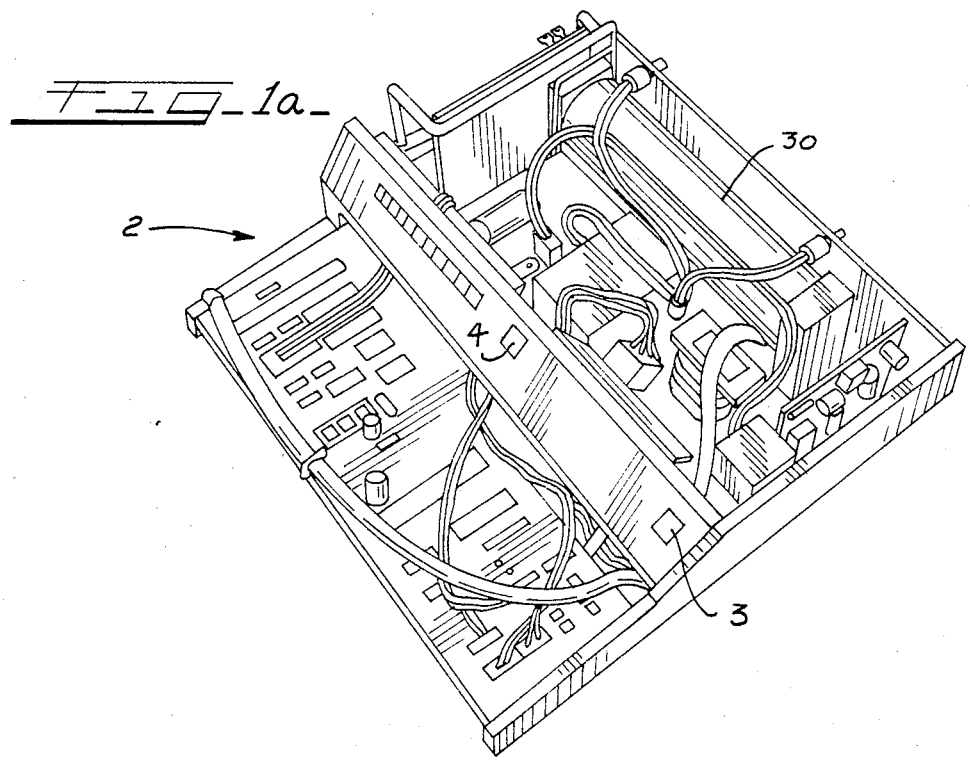
FIG_1a_
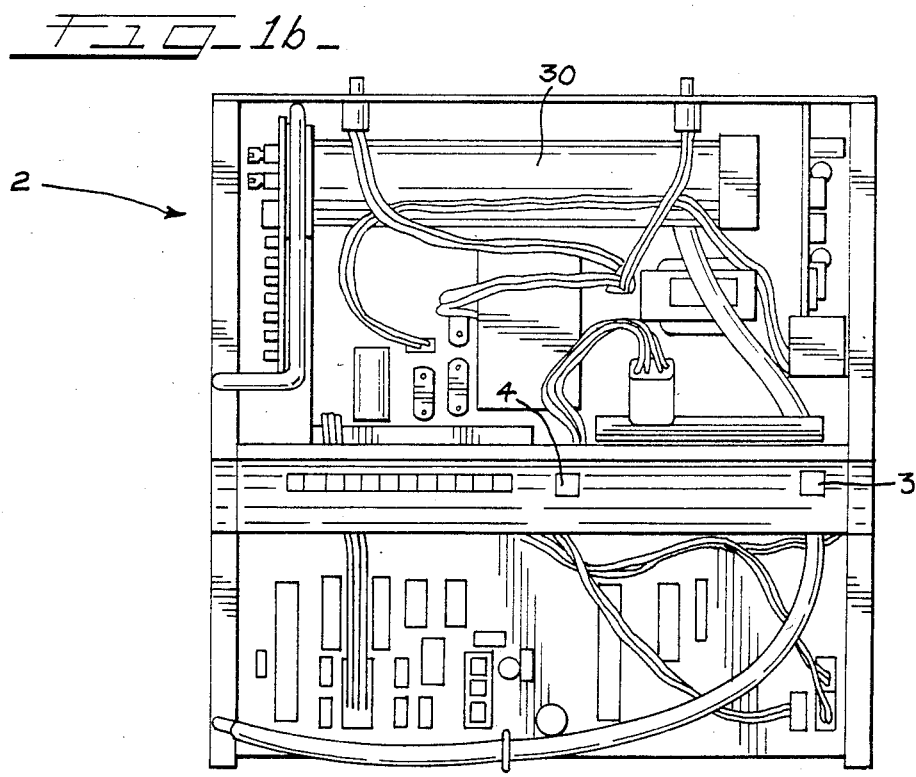
FIG_1b_

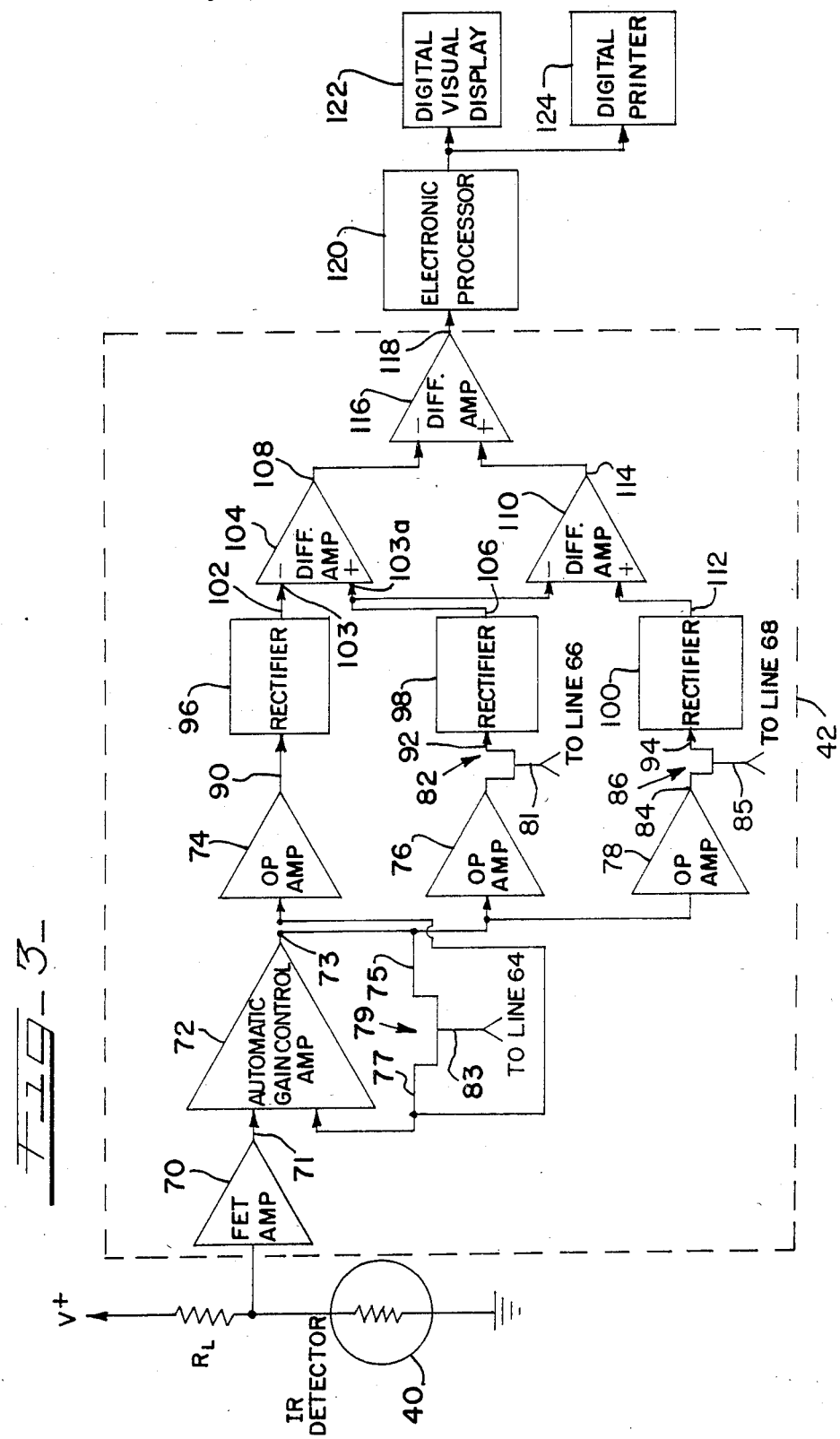

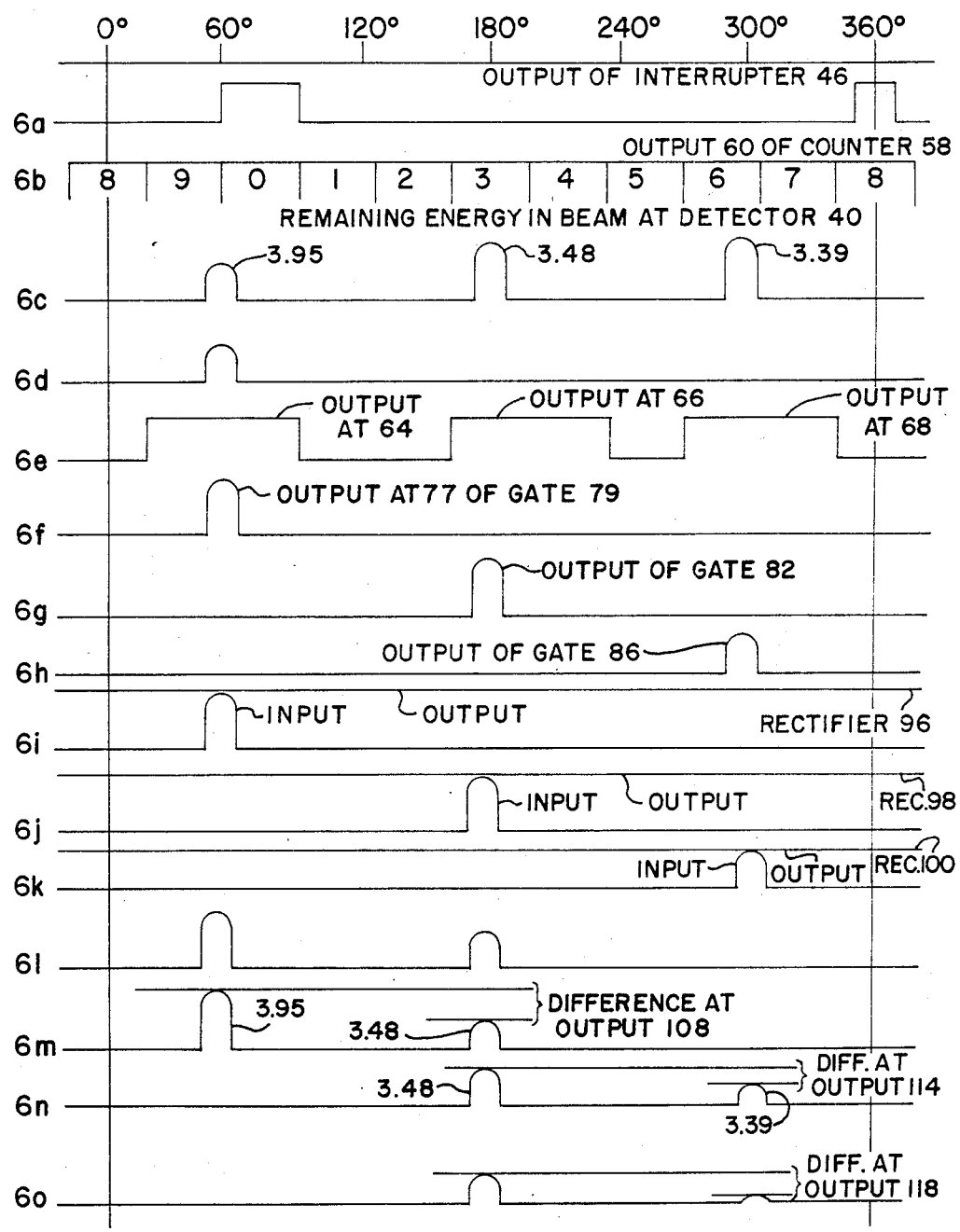

BREATH ANALYZER

BACKGROUND OF THE INVENTION

1. Field of the Invention

This invention relates generally to apparatus for detecting and measuring the concentration of an energy absorbing compound in a breath sample of a human subject. More particularly, it relates to a method and apparatus for determining only ethanol concentrations in a breath sample without the influence of commonly occurring interferants, such as acetone and water vapor.

2. Description of the Prior Art

The basic physical principles of absorption by ethanol and other materials of energy from a beam of infrared electromagnetic energy, upon which the present invention is based, is well-known in the prior art. Such a technique has been fully described and illustrated in U.S. Pat. No. 3,562,524 which issued on Feb. 9, 1971 to Donald F. Moore and is incorporated herein by reference. Heretofore, there have been many methods and apparatus in the prior art which have utilized the principles of absorption by ethanol and made practical implementations of such infrared means to measure the ethanol concentration in a breath sample.

For example, in U.S. Pat. No. 3,792,272 to Harte et al there is disclosed a system for detecting and quantifying ethanol content in a breath sample which uses a single infrared wavelength (3.39 microns). Since this single wavelength of energy is absorbed both by ethanol and other energy absorbing compounds naturally occurring in the breath sample such as acetone or ingested compounds such as turpentine, the infrared measurement will be rendered inaccurate and overstated if other energy absorbing compounds are present.

Further, there is disclosed in U.S. Pat. No. 4,268,751 to Fritzlen et al and assigned to the same assignee of the present invention a method and apparatus for detecting the possible presence of an energy absorbing compound (i.e., acetone) in a breath sample which may render inaccurate a measurement of the concentration of a predetermined energy absorbing compound (i.e., ethanol) present in the sample. Fritzlen applies two predetermined wavelengths (3.39 microns and 3.48 microns) to the same breath sample contained in a chamber, at least one of which wavelength is sufficently absorbed by ethanol. The infrared energy remaining in each of the two wavelengths after absorption by the collected sample is received by an infrared detector which converts this remaining quantity of infrared energy to an equivalent electrical signal. The equivalent electrical signal representative of the first wavelength and the equivalent electrical signal representative of the second wavelength are continuously compared and their difference is required to remain substantially constant at a predetermined value throughout the test. The lack of a predetermined comparison value indicates the presence of an infrared energy absorbing compound other than ethanol. However, Fritzlen suffers from a disadvantage in that it merely detects the presence of an unknown energy absorbing compound but cannot determine accurately the concentration of the predetermined energy absorbing compound when both the unknown energy absorbing compound and the predetermined energy absorbing compound are present in a sample. Further, Fritzlen does not compensate for the presence of water vapor which is always present in a breath sample.

Accordingly, it would be desirable to provide a breath analyzer for determining the amount of a predetermined energy absorbing compound such as ethanol in a sample even when unknown energy absorbing compounds such as acetone and water vapor are also present. The present invention provides a method and apparatus for determining only ethanol concentrations in a breath sample without the influence of occurring interferants, such as acetone and water vapor. The technique of the present invention is so general in that the concentration of any desired energy absorbing compound found in a breath sample can be determined independently of any potential interferant.

SUMMARY OF THE INVENTION

Accordingly, it is a general object of the present invention to provide an improved method and system for determining the amount of a predetermined energy absorbing compound in a sample which is relatively simple and economical to manufacture and is easy to operate, but yet overcomes the disadvantages of the prior art breath analyzers.

It is another object of the present invention to provide a system for determining the amount of a predetermined energy absorbing compound such as ethanol in a sample even when unknown energy absorbing compounds such as acetone and water vapor are also present.

It is another object of the present invention to provide a system for determining the amount of a predetermined energy absorbing compound which includes circuit means for generating an electrical output signal which is proportional only to the predetermined energy absorbing compound.

It is still another object of the present invention to provide a system for determining the amount of a predetermined energy absorbing compound such as ethanol in a sample which includes a display device responsive to an electrical output signal for indicating visually the amount of the predetermined energy absorbing compound in the sample.

It is yet still another object of the present invention to provide a method for determining the amount of the predetermined energy absorbing compound in a sample even when unknown energy absorbing compounds such as acetone and water vapor are also present.

It is yet still another object of the present invention to provide a system for indicating the presence of acetone. In accordance with the aims and objectives of the present invention, there is provided a system for determining the amount of a predetermined energy absorbing compound in a sample even when unknown energy absorbing compounds are also present and where both the predetermined energy absorbing compound and the unknown energy absorbing compounds do not absorb a first predetermined wavelength of energy and where both the predetermined energy absorbing compound and the unknown energy absorbing compounds absorb both second and third predetermined wavelengths of energy. The system includes generating means for producing a first predetermined wavelength of energy, a second predetermined wavelength of energy and a third predetermined wavelength of energy. A chamber means is provided in the path of the first, second and third predetermined wavelengths of energy for receiving the sample and for passing the first, second and third predetermined wavelengths therethrough. Detecting means is provided in the path of the first, second and third predetermined wavelengths for sensing separately the amount of energy remaining in each of the first, second and third predetermined wavelengths after the passing of the first, second and third predetermined wavelengths through the chamber means. Circuit means are responsive to the first, second and third predetermined wavelengths and is connected to the detecting means for generating an electrical output signal which is proportional to only the predetermined energy absorbing compound.

Among the major features and advantages of the present invention are that it provides a quick and reliable determination of the concentration of the ethanol in a breath sample even when unknown energy absorbing compounds such as acetone and water vapor are also present. Further, the present system is unaffected by changes that occur to the optical path, detector sensitivity, degradation of electrical components, intensity of the infrared source, small temperature deviations and humidity in the atmosphere.

Further, other features and advantages of the present invention are listed as follows:

1. It provides a direct method of measuring the ethanol concentration only even in the presence of other unknown energy absorbing compounds, without the use of chemicals.

2. The system is extremely simple to operate so as to minimize training time in its use.

3. It compensates for particulate matter in the light path such as smoke or dust.

4. There has been eliminated the requirement of high grade optics.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIG. 1a is a perspective view of a breath analyzer device embodying the principles of the present invention;

FIG. 1b is a top plan view of the present invention with the cover removed;

FIG. 3 is a detailed schematic diagram of the electronic circuit means of FIG. 2;

FIG. 6 is a timed relationship diagram of the infrared energy pulses at certain selected circuit outputs.

DETAILED DESCRIPTION OF THE PREFERRED EMBODIMENT

Referring now in detail to the various views of the drawings, there are shown in FIGS. 1a and 1b a breath analyzer device 2 embodying the features of the present invention wherein the blood alcohol content of a suspected drunk driver may be determined by analysis of the expired breath of the subject. The device 2 has an on/off push bottom power switch 3 that applies AC power thereto. With the switch 3 in the "on" position, the operating procedure for conducting a breath test involves merely a one-step operation in which the operator pushes the start test switch 4. This causes the device to automatically purge the sample chamber, analyze the breath sample of the subject, and again purge the sample chamber. This step is then repeated for the next breath test.

Figure 2:
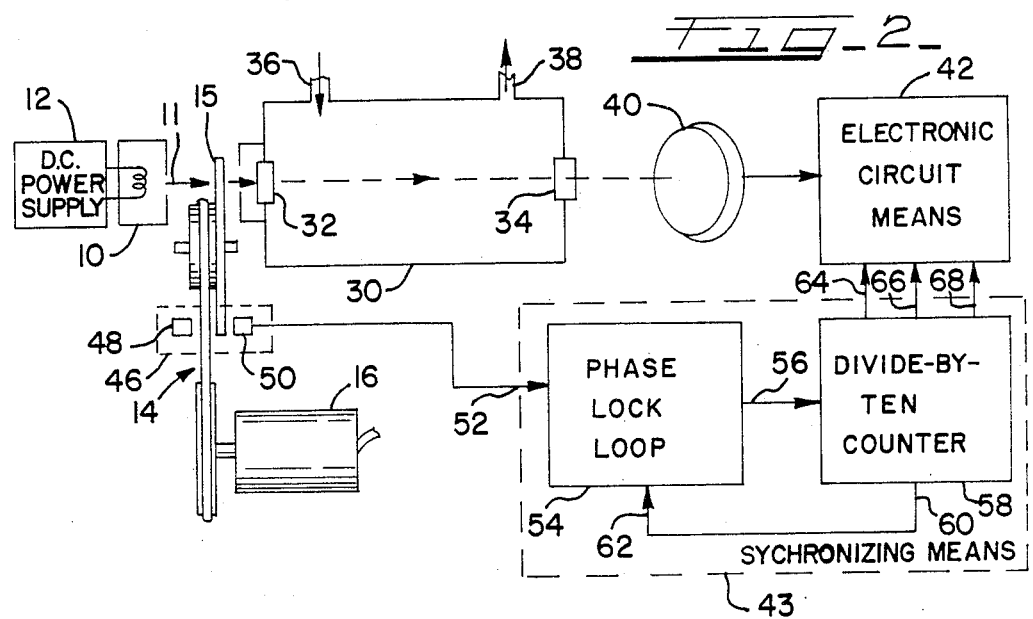
FIG. 2 is a combination block and schematic diagram of the breath analyzer device of the present invention.
Figure 4:
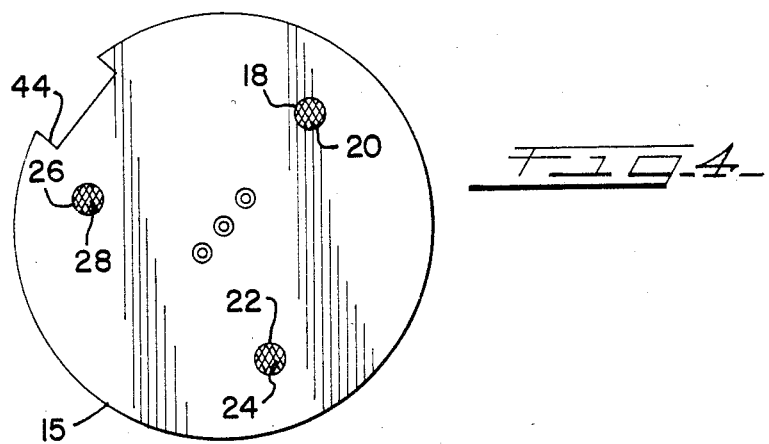
FIG. 4 is a plan view of the rotating filter wheel.

As can best be seen in FIG. 2, there is shown a block and schematic diagram of the present invention which includes an infrared source 10 controlled by a highly stable, well-regulated DC power supply 12. The source 10 consists preferably of a quartz iodine or other quartz halogen lamps. However, it should be clearly understood by those skilled in the art that many other alternative infrared sources may be used such as an incandescent lamp, helium-neon laser, or heater wires. The source 10 transmits a beam 11 of infrared energy to modulator means 14 such as a rotating filter wheel 15 driven by a motor 16. The filter wheel 15 (FIG. 4) is opaque to the beam 11 except for three distinct apertures. The first aperture 18 is covered by a narrow band optical filter 20 which is less than 4 microns. A second aperture 22 is covered by a narrow band 3.48 micron optical filter 24 and a third aperture 26 is covered by a narrow band 3.39 micron optical filter 28. The source 10 produces a broad band of energy which is one where many discrete wavelengths of energy are present. On the other hand, a narrow band of energy is defined by one which contains only a single or closely grouped wavelength.

FIGS. 6a–6o illustrate the time-related occurrence of input and output signals at various selected points in the energy detecting and electronic circuitry of the present invention. Time is conveniently expressed on the horizontal axes in degrees of filter wheel rotation which is a function of the speed of the motor 16 (revolutions per minute). The vertical axes represent the relative amplitude of the various electrical signals.

The apertures 18, 22 and 26 are formed in and equally spaced apart at 120° apart about the rotating filter wheel 15. By dividing the circumference of the filter wheel 15 into 360 degrees, the aperture 18 is considered to be at 60 degrees. The aperture 22 is at 180 degrees and the aperture 26 is at 300 degrees. As a result, the beam downstream from the filter wheel 15 will no longer be continuous but will appear as reoccuring succession of individual pulses of infrared energy separated by 120°. The first pulse will be representative of a narrow banded infrared energy of less than 4 microns. For convenience of illustration, this first pulse is selected as one of a narrow band 3.95 micron infrared energy. The first pulse will be followed by a second pulse of narrow band 3.48 micron infrared energy which will be, in turn, followed by a third pulse of narrow band 3.39 micron infrared energy. The timewise relationship of these three infrared pulses is depicted in FIG. 6c. This beam consisting of discrete pulses is transmitted through a breath sample chamber 30 by means of infrared transmitting windows 32 and 34 located at each end of the chamber. Alternatively, the filter wheel 15 may be positioned adjacent the window 34 as opposed to the window 32 as shown in FIG. 2. The chamber is formed with suitable inlet 36 and outlet 38 to introduce, store and purge the breath sample to be tested, as is well-known in the art. As the beam 11 emerges from the infrared transmitting window 34, it impinges onto an infrared detector 40 which is preferably a lead selenide photocell conductor. The infrared signals from the detector 40 are converted to electrical signals for further amplifying, electronic processing, rectifying and displaying by electronic circuit means 42.

In order to precisely locate and identify electronically each of the three separated pulses of infrared energy which are reoccurring every 360°, synchronizing means 43 includes a notch 44 formed in the filter wheel 15 which is detected electronically each revolution thereof by an interrupter circuit 46. The interrupter circuit 46 includes a light-emitting diode (LED) 48 and a photo-transistor 50 which generates a pulse each time the notch 44 on the wheel 15 is passed therethrough. The signal at the output of the interrupter 46 is illustrated by FIG. 6a. These pulses are sent to the input 52 of a phase lock loop 54. The phase lock loop is preferably an IC type 4046 which is manufactured and sold by RCA Corporation. Only the significant parts of the phase lock loop are illustrated in block form in FIG. 2. For a full understanding of the principles and the means for selecting component values to fully implement IC 4046 in the present application, application note ICAN 6101 in the SSD-203C 1975 Databook Series published by RCA Corporation is hereby incorporated by reference. The output 56 of the phase lock loop is frequency divided by ten by means of a divide-by-ten counter 58. The output 60 of the counter 58 is applied to a second input 62 of the phase lock loop so as to synchronize the leading edge of the 3.95 micron energy pulse at the input 52 with every fourth pulse of the output 56. The signal at the output 60 of the counter 58 is shown in FIG. 6b. By selecting the appropriate outputs 64, 66 and 68 of the counter 58, there will be produced three pulses or time windows separated by 120°. These three separate time windows appearing at outputs 64, 66 and 68 have been combined and are illustrated in FIG. 6e.

Referring now to FIG. 3, the electronic circuit means 42 includes a very high input impedance field-effect transistor (FET) amplifier 70 which serves as a detector load for the electrical signal consisting of all three infrared pulses, (FIG. 6c) namely, the pulses representing the energy remaining in the 3.95 micron wavelength, the 3.48 micron wavelength and the 3.39 micron wavelength from the detector 40. The output 71 of the FET amplifier 70 is delivered to an automatic gain control (AGC) amplifier 72 whose output 73 is further fed back to the other input of the amplifier 72 via the input 75 and output 77 of a FET gate 79. The output 77 of the gate 79 is connected to the input of a stable low noise operational amplifier 74 referred to hereinafter as the 3.95 or reference channel. The output 73 of the AGC amplifier 72 is also connected to the inputs of a second operational amplifier 76 hereinafter referred to as the 3.48 channel and a third operational amplifier 78 hereinafter referred to as the 3.39 channel. The other input 83 of the FET gate 79 is controlled by the time window output 64 of the counter 58. Therefore, the signal levels to the amplifiers 74, 76 and 78 are affected only by those factors which are common to all three windows, i.e., temperature, particulate matter or component drift.

The output of the second operational amplifier 76 is fed to the input of a FET gate 82 whose other input 81 is controlled by time window output 66 of the counter 58. Thus, the output of the gate 82 will produce signals representing the energy remaining in the 3.48 micron wavelength only when the time window output 66 and the 3.48 infrared pulse occur simultaneously. Similarly, the output 84 of the third operational amplifier 78 is fed to the input of a FET gate 86 whose other input 85 is controlled by the time window output 68 of the counter 58. Therefore, the output of the gate 86 will produce a signal representing the energy remaining in the 3.39 micron wavelength only when the time window output 68 and the 3.39 infrared pulse occur simultaneously.

The output 77 of the gate 79 provides a signal representing the energy remaining in the 3.95 micron wavelength when the time window output 64 and the 3.95 infrared pulse occur simultaneously. The output 77 of the gate 79 is depicted by FIG. 6f. The output of the gate 82 is shown in FIG. 6g and the output of the gate 86 is shown in FIG. 6h. Thus, it can be seen the infrared energy remaining in the 3.95, 3.48 and 3.39 wavelengths have been completely separated into individual pulses.

The outputs 90, 92 and 94 of the respective 3.95 channel, 3.48 channel and 3.39 channel are connected to conventional rectifiers 96, 98 and 100 to convert their pulse amplitude signal to a DC voltage which is proportional to the amount of energy remaining in the 3.95, 3.48 and 3.39 wavelengths after their passing through the breath sample. FIGS. 6i, 6j and 6k illustrate both the pulses and the inputs of the rectifiers 96, 98 and 100 and the DC voltages at the outputs of the rectifiers whose amplitudes are proportional to the peak amplitudes of the pulses on the rectifier inputs. The operational amplifiers 74, 76 and 78 are essentially identical circuits so that the proportionality of the energy remaining in the three wavelengths is electrically preserved.

For the purposes of discussion, the 3.95 micron wavelength for the reference channel is insensitive or is not absorbed by all potential infrared energy absorbing compounds. In this preferred embodiment, there are shown to be three channels. However, it should be apparent to those skilled in the art that any number of channels could be selected as desired. In the present invention, a first channel is for a reference, a second channel is for ethanol and a third channel is for acetone. As can best be seen from FIG. 3, the output 102 of the rectifier 96 connected to the reference channel is connected to one input of a first differential amplifier 104, and the output 106 of the rectifier 98 connected to the ethanol channel is connected to the other input of the differential amplifier 104. Since the reference channel has been selected to be insensitive to all potential infrared energy absorbing compounds, the input 102 of the amplifier 104 should remain at a constant predetermined value. Any deviation from this by the input 102 would indicate that there is an error in the system or an environmental change. Since acetone is also absorbed in the ethanol channel, the input 103a of the amplifier 104 would be proportional to the energy remaining after absorption by both ethanol and acetone. Thus, the output 108 of the amplifier 104 is proportional to the ethanol and acetone concentration assuming the reference signal remains constant. The output 108 of the first differential amplifier 104 is shown in FIG. 6l when only ethanol is present. The output 108 is shown in FIG. 6m when both ethanol and acetone are present.

The output 106 of the rectifier 98 connected to the ethanol channel is also connected to one input of a second differential amplifier 110, and the output 112 of the rectifier 100 connected to the acetone channel is coupled to the other input of the second differential amplifier 110. The gain of the acetone channel 78 amplifier is adjusted so that the output 114 of the amplifier 110 is zero when ethanol only is introduced in the sample chamber. Thus, the output 114 will not change when ethanol only is present in the sample chamber but there will be a change when acetone is introduced.

When acetone is present, the change at output 114 will be proportional to the change at output 108. The output 114 of the second differential amplifier 110 is shown in FIG. 6n.

The output 114 of the second differential amplifier 110 is connected to one input of a third differential amplifier 116, and the output 108 of the first differential amplifier 104 that is proportional to the ethanol and acetone concentration is connected to the other input of the differential amplifier 116. The amplifier 116 defines an ethanol-acetone subtractor amplifier which subtracts the signal that is proportional to acetone from the signal that is proportional to the ethanol and acetone concentration. Thus, the output 118 of the third differential amplifier 116 will not change when only acetone is in the chamber, but there will be a change when ethanol is introduced. Accordingly, the output signal 118 will be proportional to the ethanol concentration. The output 118 of the third differential amplifier 116 is shown in FIG. 6o.

Figure 5:
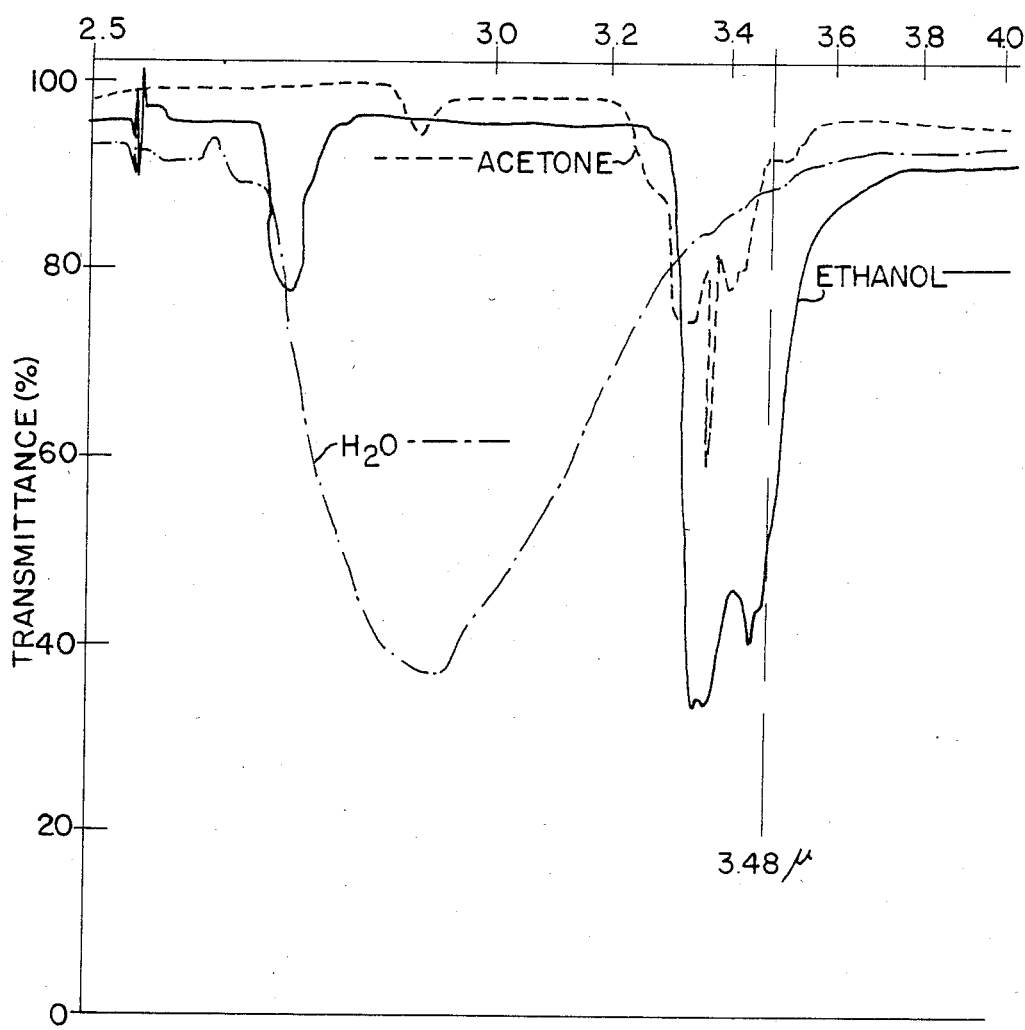
FIG. 5 is a plot of the relative absorption of infrared energy by ethanol, water vapor and acetone at wavelengths between 2.5 microns and 4.0 microns.

It should be understood that if the acetone channel having a 3.39 wavelength of energy was appropriately selected to be one in which water vapor is also absorbed in this acetone channel then the output signal 118 would also cancel out the effect of water vapor. Alternatively, the reference channel having the 3.95 wavelength of energy could be selected appropriately to be sensitive only to water vapor, then the output signal would still be proportional only to the ethanol concentration subtracting out the effect of water vapor. For the purposes of illustration, FIG. 5 depicts the relative absorption response of ethanol, acetone and water vapor in the three specific wavelengths of 3.39, 3.48 and 3.95 microns used in this preferred embodiment.

The output signal 118 is a rectified DC signal which has an electrical value proportional to the amount of ethanol in a collected breath sample even when other unknown energy absorbing compounds are present. The output signal 118 is fed to an electronic processor 120 which converts this electrical value to a digital form that may be scaled to Blood Alcohol Content (BAC) or any other desired scale. The output of the electronic processor 120 drives a Digital Visual display 122 such as a seven-segment light-emitting diode display to indicate the BAC value and/or a digital printer 124.

From the foregoing detailed description, it can thus be seen that the present invention provides an improved method and system for determining the amount of a predetermined energy absorbing compound in a breath sample even when unknown energy absorbing compounds are also present. Specifically, there are provided a method and apparatus for determining only ethanol concentrations in a breath sample without the influence of occurring interferants, such as acetone and water vapor.

While there has been illustrated and described what is at present to be the preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out this invention, but that the invention will include all embodiments falling within the scope of the appended claims.

What is claimed is:

1. A system for determining the amount of a predetermined energy absorbing compound in a sample when unknown energy absorbing compounds are also present and where both the predetermined energy absorbing compound and the unknown energy absorbing compounds absorb both first and second predetermined wavelengths of energy, said system comprising, in combination, generating means for producing a first predetermined wavelength of energy and a second predetermined wavelength of energy, both said first predetermined wavelength and said second predetermined wavelength being absorbed by both the predetermined energy absorbing compound and the unknown energy absorbing compounds when both are present in the sample, chamber means in the paths of said first and second predetermined wavelengths of energy for receiving the sample and for passing said first and second predetermined wavelengths therethrough;

detecting means in the path of said first and second predetermined wavelengths for producing a first signal proportional to the energy remaining in said first predetermined wavelength and a second signal proportional to the energy remaining in said second predetermined wavelength after each has been absorbed by said predetermined energy absorbing compound and said unknown energy absorbing compounds, first circuit means for receiving said first signal, second circuit means for receiving both said first signal and said second signal and for subtracting them to produce a third signal, said second circuit means being adjusted so that said third signal is constant when only said predetermined energy absorbing compound is in said chamber whereby said third signal will be proportional to said unknown energy absorbing compounds in said sample, and third circuit means for receiving said first signal and said third signal and subtracting them to produce an electrical output which is proportional to said predetermined energy absorbing compound in said sample.

2. A system as defined in claim 1 where said sample is a breath sample, said predetermined energy absorbing compound is ethanol, and an unknown energy absorbing compound is acetone.

3. A system as defined in claim 1 where said sample is a breath sample, said predetermined energy absorbing compound is ethanol, and said unknown energy absorbing compounds are acetone and water vapor.

4. A system as defined in claim 1 where said first signal is submitted to a first differential amplifier, said first and second signals are submitted to a second differential amplifier which produces said third signal, said third signal being constant when only said predetermined energy absorbing compound is in said sample, and said third signal being conducted to said first differential amplifier which subtracts said third signal from said first signal to produce said electrical output proportional to said predetermined energy absorbing compound in said sample.

5. A system as defined in claim 1 where said generating means includes an infrared energy source producing a broad band of wavelengths, and filter means for passing separately said first and second predetermined wavelengths.

6. A system as defined in claim 1 where said second circuit means is adjusted so said third signal is zero when only said predetermined energy absorbing compound is in said chamber.

7. A system for determining the amount of a predetermined energy absorbing compound in a sample when unknown energy absorbing compounds are also present and where both the predetermined energy absorbing compound and the unknown energy absorbing compounds absorb both first and second predetermined wavelengths of energy, said system comprising, in combination, generating means for producing a first predetermined wavelength of energy and a second predetermined wavelength of energy, both said first predetermined wavelength and said second predetermined wavelength being absorbed by both the predetermined energy absorbing compound and the unknown energy absorbing compounds when both are present in the sample,
chamber means in the paths of said first and second predetermined wavelengths of energy for receiving the sample and for passing said first and second predetermined wavelengths therethrough,
detecting means in the path of said first and second predetermined wavelengths for producing a first signal proportional to the energy ramaining in said first predetermined wavelength and a second signal proportional to the energy remaining in said second predetermined wavelength after each has been absorbed by said predetermined energy absorbing compound and said unknown energy absorbing compounds,
first rectifier means for receiving said first signal, second rectifier means for receiving said second signal, first differential amplifier means for receiving said first signal from said first rectifier means, second differential amplifier means for receiving said first signal from said first rectifier means and said second signal from said second rectifier means and for subtracting them to produce a third signal,
means for adjusting one of said first and second signals so that said third signal is constant when only said predetermined energy absorbing compound is in said chamber whereby said third signal will be proportional to said unknown energy absorbing compounds in said sample, and means for conducting said third signal to said first differential amplifier means, said first differential amplifier means subtracting said third signal from said first signal to produce an electrical output which is proportional to said predetermined energy absorbing compound in said sample.

8. A system as defined in claim 7 where said means for adjusting one of said first and second signals comprises an operational amplifier connected to the corresponding one of said first and second rectifier means, said operational amplifier being adjusted so said third signal is zero when only said predetermined energy absorbing compound is in said chamber.

9. A system as defined in claim 7 where said sample is a breath sample, said predetermined energy absorbing compound is ethanol, and an unknown energy absorbing compound is acetone.

10. A system as defined in claim 7 where said sample is a breath sample, said predetermined energy absorbing compound is ethanol, and said unknown energy absorbing compounds are acetone and water vapor.

11. A system as defined in claim 7 where said generating means includes an infrared energy source producing a broad band of wavelengths, and filter means for passing separately said first and second predetermined wavelengths.

12. A system as defined in claim 7 including first gating means for controlling the transmission of said first signal to said first rectifier means and second gating means for controlling the transmission of said second signal to said second rectifier means.

13. A system as defined in claim 7 where said means for adjusting one of said first and second signals is adjusted so said third signal is zero when only said predetermined energy absorbing compound is in said chamber.

14. A system for determining the amount of a predetermined energy absorbing compound in a sample when unknown energy absorbing compounds are also present and where both the predetermined energy absorbing compound and the unknown energy absorbing compounds do not absorb a first predetermined wavelength of energy and where both the predetermined energy absorbing compound and the unknown energy absorbing compounds absorb both second and third predetermined wavelengths of energy, said system comprising, in combination, generating means for producing a first predetermined wavelength of energy, a second predetermined wavelength of energy and a third predetermined wavelength of energy, said first predetermined wavelength of energy being unabsorbed by the predetermined energy absorbing compound and the unknown energy absorbing compounds, both said second predetermined wavelength and said third predetermined wavelength being absorbed by both the predetermined energy absorbing compound and the unknown energy absorbing compounds when both are present in the sample,
chamber means in the paths of said first, second and third predetermined wavelengths of energy for receiving the sample and passing said first, second and third predetermined wavelengths therethrough,
detecting means in the path of said first, second and third predetermined wavelengths for producing a first signal proportional to the energy remaining in said first predetermined wavelength, a second signal proportional to the energy remaining in said second predetermined wavelength and a third signal proportional to the energy remaining in said third predetermined wavelength after each has passed through said chamber,
first circuit means for receiving said first and second signals and subtracting them to produce a fourth signal proportional to the energy remaining in said second signal after absorption by said predetermined energy absorbing compound and said unknown energy absorbing compounds,
second circuit means for receiving said second and third signals and subtracting them to produce a fifth signal, said second circuit means being adjusted so that said fifth signal is constant when only said predetermined energy absorbing compound is in said chamber whereby said fifth signal will be proportional to said unknown energy absorbing compounds in said sample, and third circuit means for receiving said fourth signal and said fifth signal and subtracting them to produce an electrical output which is proportional to said predetermined energy absorbing compound in said sample.

15. A system as defined in claim 14 where said sample is a breath sample, said predetermined energy absorbing compound is ethanol, and an unknown energy absorbing compound is acetone.

16. A system as defined in claim 14 where said sample is a breath sample, said predetermined energy absorbing compound is ethanol, and said unknown energy absorbing compounds are acetone and water vapor.

17. A system as defined in claim 14 where said first signal and second signals are transmitted to a first differential amplifier which subtracts them to produce said fourth signal, said second and third signals are transmitted to a second differential amplifier which subtracts them to produce said fifth signal, said fifth signal being constant when only said predetermined energy absorbing compound is in said chamber, and said fourth and fifth signals are transmitted to a third differential amplifier which subtracts them to produce said electrical output proportional to said predetermined energy absorbing compound in said sample.

18. A system for determining the amount of a predetermined energy absorbing compound in a sample when unknown energy absorbing compounds are also present and where both the predetermined energy absorbing compound and the unknown energy absorbing compounds do not absorb a first predetermined wavelength of energy and where both the predetermined energy absorbing compound and the unknown energy absorbing compounds absorb both second and third predetermined wavelengths of energy, said system comprising, in combination, generating means for producing a first predetermined wavelength of energy, a second predetermined wavelength of energy and a third predetermined wavelength of energy, said first predetermined wavelength of energy being unabsorbed by the predetermined energy absorbing compound and the unknown energy absorbing compounds, both said second predetermined wavelength and said third predetermined wavelength being absorbed by both the predetermined energy absorbing compound and the unknown energy absorbing compounds when both are present in the sample, chamber means in the paths of said first, second and third predetermined wavelengths for producing a first signal proportional to the energy remaining in said first predetermined wavelength, a second signal proportional to the energy remaining in said second predetermined wavelength, and a third signal proportional to the energy remaining in said third predetermined wavelength after each has passed through said chamber, first rectifier means for receiving said first signal, second rectifier means for receiving said second signal, third rectifier means for receiving said third signal, first differential amplifier means for receiving said first and second signals from said first and second rectifier means and subtracting them to produce a fourth signal proportional to the energy remaining in said second signal after absorption by said predetermined energy absorbing compound and said unknown energy absorbing compounds, second differential amplifier means for receiving said second and third signals from said second and third rectifier means and for subtracting them to produce a fifth signal, means for adjusting one of said second and third signals so that said fifth signal is constant when only said predetermined energy absorbing compound is in said chamber whereby said fifth signal will be proportional to said unknown energy absorbing compounds in said sample, and a third differential amplifier means for receiving said fourth and fifth signals and subtracting them to produce an electrical output proportional to said predetermined energy absorbing compound in said sample.

19. A system as defined in claim 18 where said means for adjusting one of said second and third signals comprises an amplifier connected to the corresponding one of said second and third rectifier means, said amplifier being adjusted so that said fifth signal is zero when only said predetermined energy absorbing compound is in said chamber.

20. A system as defined in claim 18 where said sample is a breath sample, said predetermined energy absorbing compound is ethanol, and an unknown energy absorbing compound is acetone.

21. A system as defined in claim 18 where said sample is a breath sample, said predetermined energy absorbing compound is ethanol, and said unknown energy absorbing compounds are acetone and water vapor.

22. A system as defined in claim 18 where said generating means includes an infrared energy source producing a broad band of wavelengths, and filter means for passing separately said first, second and third predetermined wavelengths.

23. A system as defined in claim 18 including first gating means for controlling the transmission of said first signal to said first rectifier means, second gating means for controlling the transmission of said second signal to said second rectifier means, and third gating means for controlling the transmission of said third signal to said third rectifier means.

24. A system as defined in claim 18 where said means for adjusting one of said second and third signals is adjusted so said fifth signal is zero when only said predetermined energy absorbing compound is in said chamber.

25. A method for determining the amount of a predetermined energy absorbing compound in a sample even when unknown energy absorbing compounds are also present and where both the predetermined energy absorbing compound and the unknown energy absorbing compounds absorb both first and second predetermined wavelengths of energy, said method comprising the steps of:

generating a first predetermined wavelength of energy and a second predetermined wavelength of energy, both said first predetermined wavelength and said second predetermined wavelength being absorbed by both the predetermined energy absorbing compound and the unknown energy absorbing compounds when both are present in the sample, passing said first and second predetermined wavelengths through the sample, detecting separately the amount of energy remaining in each of said first and second predetermined wavelengths after passing through the sample so as to produce a first signal proportional to the energy remaining in said first predetermined wavelength and a second signal proportional to the energy remaining in said second predetermined wavelength after each has been absorbed by said predetermined energy absorbing compound and said unknown energy absorbing compounds, subtracting one of said first and second signals from the other and producing a third signal, adjusting said third signal to be constant when only said predetermined energy absorbing compound is present in the sample whereby said third signal will be proportional to said unknown energy absorbing compounds in said sample, and subtracting said third signal from said first signal to produce an electrical output which is proportional to said predetermined energy absorbing compound in said sample.

26. A method as defined in claim 25 where said third signal is adjusted to be zero when only said predetermined energy absorbing compound is present in the sample.

27. A method as defined in claim 25 where said predetermined energy absorbing compound is ethanol, and an unknown energy absorbing compound is acetone.

28. A method as defined in claim 25 where said sample is a breath sample, said predetermined energy absorbing compound is ethanol, and said unknown energy absorbing compounds are acetone and water vapor.

29. A method for determining the amount of a predetermined energy absorbing compound in a sample when unknown energy absorbing compounds are also present and where both the predetermined energy absorbing compound and the unknown energy absorbing compounds do not absorb a first predetermined wavelength of energy and where both the predetermined energy absorbing compounds and the unknown energy absorbing compounds absorb both second and third predetermined wavelengths of energy, said method comprising the steps of:

generating a first predetermined wavelength of energy, a second predetermined wavelength of energy and a third predetermined wavelength of energy, said first predetermined wavelength of energy being unabsorbed by the predetermined energy absorbing compound and the unknown energy absorbing compounds, both said second predetermined wavelength and said third predetermined wavelength being absorbed by both the predetermined energy absorbing compound and the unknown energy absorbing compounds when both are present in the sample, passing said first, second and third predetermined wavelengths through the sample, detecting separately the amount of energy remaining in each of said first, second and third predetermined wavelengths after passing through the sample so as to produce a first signal proportional to the energy remaining in said first predetermined wavelength, a second signal proportional to the energy remaining in said second predetermined wavelength and a third signal proportional to the energy remaining in said third predetermined wavelength, subtracting one of said first and second signals from the other to produce a fourth signal proportional to the energy remaining in said second signal after absorption by said predetermined energy absorbing compound and said unknown energy absorbing compounds, subtracting one of said second and third signals from one another to produce a fifth signal, adjusting said fifth signal to be constant when only said predetermined energy absorbing compound is present in the sample whereby said fifth signal will be proportional to said unknown energy absorbing compounds in said sample, and subtracting said fifth signal from said fourth signal to produce an electrical output which is proportional to said predetermined energy absorbing compound in said sample.

30. A method as defined in claim 29 where said fifth signal is adjusted to be zero when only said predetermined energy absorbing compound is present in the sample.

31. A method as defined in claim 24 where said sample is a breath sample, said predetermined energy absorbing compound is ethanol, and an unknown energy absorbing compound is acetone.

32. A method as defined in claim 29 where said sample is a breath sample, said predetermined energy absorbing compound is ethanol, and said unknown energy absorbing compounds are acetone and water vapor.

* * * * *